United States Patent [19]

Tsunoda et al.

[11] 4,019,907
[45] Apr. 26, 1977

[54] PHOTOSENSITIVE AZIDO COLOR-FORMING ELEMENT

[75] Inventors: Takahiro Tsunoda, Funabashi; Minoru Ozutsumi, Tokyo; Shigeo Maeda, Tokyo; Susumu Suzuka, Tokyo; Hidetoshi Komiya, Tokyo; Hideaki Shinohara, Tokyo, all of Japan

[73] Assignees: Hodogaya Chemical Co., Ltd.; Oji Paper Co., Ltd., both of Tokyo, Japan

[22] Filed: Oct. 17, 1974

[21] Appl. No.: 515,571

[30] Foreign Application Priority Data

Oct. 24, 1973 Japan .................... 48-119543
July 8, 1974 Japan ................... 49-77407

[52] U.S. Cl. ................................. 96/75; 96/33; 96/36.2; 96/36.3; 96/49; 96/85; 96/86 R; 96/86 P; 96/87 R; 96/91 N; 96/115 R; 260/349

[51] Int. Cl.² ...................... G03F 7/08; G03C 1/52

[58] Field of Search .......... 96/91 N, 75, 33, 91 R, 96/49; 260/349

[56] References Cited

UNITED STATES PATENTS

| | | | |
|---|---|---|---|
| 1,760,780 | 9/1927 | Schmidt et al. | 96/91 R |
| 1,845,989 | 2/1932 | Schmidt et al. | 96/91 N |
| 2,690,968 | 10/1954 | Powers, Jr. | 96/91 N |
| 2,692,826 | 10/1954 | Neugebauer et al. | 96/91 N |
| 3,062,650 | 11/1962 | Sagura et al. | 96/90 |
| 3,092,494 | 6/1963 | Sus et al. | 96/33 |
| 3,174,860 | 3/1965 | Sus et al. | 96/33 |
| 3,235,383 | 2/1966 | Steppan et al. | 96/91 R |
| 3,679,419 | 7/1972 | Gillich | 96/91 R |
| 3,844,793 | 10/1974 | Singh | 96/91 N |
| 3,856,531 | 12/1974 | Grisdale et al. | 96/91 N |
| 3,867,147 | 2/1975 | Teuschev | 96/91 R |

OTHER PUBLICATIONS

Kosar; Light Sensitive Systems, 1935; pp. 203, 208 and 330-334.

*Primary Examiner*—Charles L. Bowers, Jr.
*Attorney, Agent, or Firm*—Paul & Paul

[57] ABSTRACT

A photosensitive color-forming element comprises a support and a photosensitive color-forming layer formed on said support and containing therein at least one photosensitive color-forming azido compound of the formula

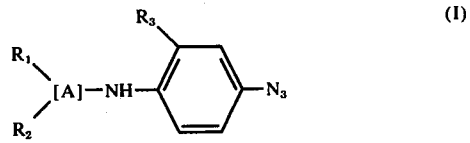

wherein
[A] is a benzene ring or naphthalene ring, $R_1$ and $R_2$ each is a hydrogen or halogen atom or alkyl, alkoxyl, dialkylamino, acyl, acylamino, nitro or hydroxyl radical, and $R_3$ is a hydrogen or halogen atom, or alkyl, alkoxyl, nitro, carboxyl, alkylcarboxyl, dialkylcarbamoyl, sulfonic acid, dialkylaminosulfonyl, alkylsulfonyl or acyl radical or a group of the formula (II), (III), (IV) or (V):

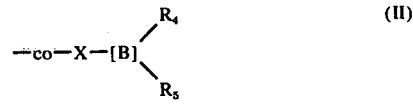

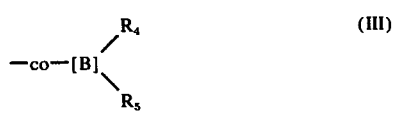

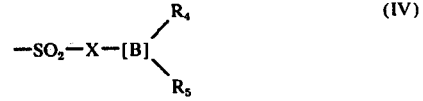

or

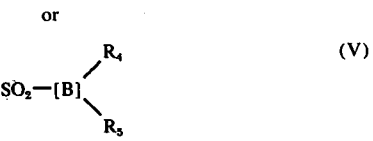

in which formula
X is an —O— bonding or —NH— bonding.
[B] is a benzene ring or naphthalene ring, and $R_4$ and $R_5$ each is a hydrogen or halogen atom or alkyl, alkoxyl, dialkylamino, acyl, acylamino or nitro radical, the photosensitive azido compound being capable of forming a dark color and hardening or solvent-non-solubilizing polymeric material, for example, novolak resins, by exposure to radiation ray.

12 Claims, No Drawings

PHOTOSENSITIVE AZIDO COLOR-FORMING ELEMENT

The present invention relates to a photosensitive color-forming element. More particularly, the present invention relates to a photosensitive color-forming element having a photosensitive color-forming layer containing special azido compounds and carried on a support.

It is well known that black images can be obtained by utilizing silver halides in photography. However, this type of photography is disadvantageously expensive because the silver halides are expensive. It is also known that a two-component diazo composition consisting of a diazonium salt and a coupler which is capable of forming an azu dye by reacting with the diazonium salt in an alkaline condition, is usable for producing color images in photography. The components of the two-component diazo composition were disclosed in detail in Kosar's "Light-Sensitive System," chapter 6, published in 1965 by John Wiley & Sons, New York. This type of photography has the disadvantages that the back-ground of the photographic element is possibly stained by deterioration products of the diazo composition during a storage period and that the developer for the diazo composition is required to contain ammonia which is harmful to the human body.

Further, it is known that a composition containing a photosensitive complex consisting of an organic azido compound such as aryl azidos and heterocyclic azidos and a third-organic phosphine and a dye-forming coupler, is usable in photography. In this type of photographic composition, the azido complex can produce color only by reacting with the dye-forming coupler, and not independently. That is, a photosensitive azido compound which can produce dark color by itself only when exposed to radiation rays, for example, light and ultra-violet rays, has not yet been discovered.

Some types of azido compounds are usable for preparing a photosensitive composition which is used to produce a photo-resist for etching or photo-relief for printing. This photosensitive composition contains the conventional azido compound as a photosensitive component and a resinous material, for example, styrenebutadiene copolymers, cyclized rubbers and novolak resins, which is capable of hardening or being insolubilized in solvent by exposure to radiation rays. However, such types of conventional photosensitive compositions are unsatisfactory in photo-hardening properties and the photosensitivity thereof. Accordingly, in order to completely harden or insolubilize a conventional photosensitive composition, it is necessary to increase the dose of the radiation rays to be directed to the photosensitive composition, add an additive to the composition for promoting the photosensitivity of the composition or increase the amount of the azido compound to be contained in the composition. These requirements make practical utilization of the conventional photosensitive composition disavantageous.

An object of the present invention is to provide a photosensitive color-forming element including therein a photosensitive azido compound which is capable of forming dark color by itself only when exposed to radiation rays.

Another object of the present invention is to provides a photosensitive color-forming element capable of being developed with a developer consisting of, for example, an aqueous solution of sodium hydroxide or sodium metasilicate which is not harmful to the human body.

Another object of the present invention is to provide a photosensitive color-forming element which is relatively cheap.

The above-mentioned objects are accomplished by the photosensitive color-forming element of the present invention which comprises a support and a photosensitive color-forming layer formed on said support and containing therein at least one photosensitive color-forming azido compound of the formula

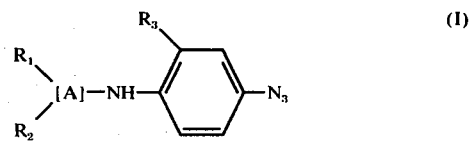

wherein

[A] represents either a benzene ring or naphthalene ring, $R_1$ and $R_2$ respectively represent a substituent selected from the group consisting of hydrogen and halogen atoms and alkyl, alkoxyl, dialkylamino, acyl, acylamino, nitro and hydroxyl radicals, and $R_3$ represents a substituent selected from the group consisting of hydrogen and halogen atoms, alkyl, alkoxyl, nitro, carboxyl, alkylcarboxyl, dialkylcarbmoyl, sulfonic acid, dialkylaminosulfonyl, alkylsulfonyl and acyl radicals and groups of the formulae (II), (III), (IV) and (V):

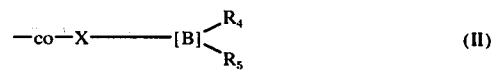

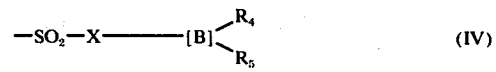

and

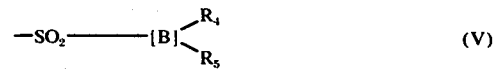

in which formulae

X represents either a —O— bonding or —NH— bonding, [B] represent either a benzene ring or naphthalene ring, and $R_4$ and $R_5$ represent respectively a substituent selected from the group consisting of hydrogen and halogen atoms and alkyl, alkoxyl, dialkylamino, acyl, acylamino and nitro radicals.

Regarding the $R_1$ and $R_2$ in the azido compound of the formula (I), it is preferable that the alkyl radical as the $R_1$ and $R_2$ has 1 to 4 carbon atoms, the alkoxy radical has 1 to 4 carbon atoms, the alkyl group in the dialkylamino radical has 1 to 4 carbon atoms, the acyl radical has 2 to 7 carbon atoms and the acyl group in the acylamino radical has 2 to 7 carbon atoms.

Also, regarding the $R_3$ in the formula (I), it is preferable that the alkyl radical as the $R_3$ has 1 to 4 carbon atoms, the alkoxyl radical has 1 to 4 carbon atoms, the alkyl groups in the alkylcarboxyl, dialkylcarbamoyl, dialkylamino-sulfonyl and alkylsulfonyl radicals have 1 to 4 carbon atoms, and the acyl radical has 2 to 7 carbon atoms.

Further, concerning the $R_4$ and $R_5$ in the formulae (II), (III), (IV) and (V), the alkyl radical as the $R_4$ and $R_5$ has 1 to 4 carbon atoms, the alkoxyl radical 1 to 4 carbon atoms, the alkyl groups in the dialkylamino 1 to 4 carbon atoms, the acyl radical 2 to 7 carbon atoms and the acyl group in the acylamino radical 2 to 7 carbon atoms.

The photosensitive azido compound usable for the present invention produces a dark color, for example, black, dark brown, brown dark green, and dark blue-black when it is exposed to radiation rays such as visible light and ultra-violet rays.

In the case where the [A] moiety in the photosensitive color-forming azido compound of the formula (I) is a benzene ring, the $R_1$ and $R_2$ substituents may be in 2- and 4- positions, 3- and 5- positions or 2- and 5-positions of the benzene ring [A] with respect to the -NH- group on the benzene ring [A].

The above type of the photosensitive azido compound may be selected from the group consisting of the compounds listed below. In the following list, the color of the exposed and color-formed azido compound is shown in parenthesis after the name of the compound.

2-phenylamino-5-azido, benzoic acid (black),
methyl ester of 2-anilino-5-azido benzoic acid (dark green),
2-(4'-nitrophenyl)amino-5-azidobenzoic acid (yellow),
2-(4'-chlorophenyl)amino-5-azidobenzoic acid (dark grey),
2-(4'-hydroxyphenyl)amino-5-azidobenzoic acid (black),
2-(4'-methylphenyl)amino-5-azidobenzoic acid (black),
2-(4'-methoxyphenyl)amino-5-azidobenzoic acid (black),
2-(4'-diethylaminophenyl)amino-5-azidobenzoic acid (black),
2-(2'-methylphenyl)amino-5-azidobenzoic acid (black),
2-(4'-acetylphenyl)amino-5-azidobenzoic acid (dark grey),
2-(2',5'-dimethoxyphenyl)amino-5-azidobenzoic acid (black),
2-(2'-hydroxyl-4'-methylphenyl)amino-5-azidobenzoic acid (black),
2-(4'-methoxyphenyl)amino-5-azidobenzoic acid (black),
methyl ester of 2-(4'-methoxyphenyl)amino-5-azidobenzoic acid (black),
ethyl ester of 2-(2',4'-dimethylphenyl)amino-5-azidobenzoic acid (dark green),
ethyl ester of 2-(4'-acetaminophenyl)amino-5-azidobenzoic acid (dark green),
2-(4'-methylphenyl)amino-5-azidotoluene (dark green),
2-(4'-chlorophenyl)amino-5-azidoanisole (dark grey),
2-phenylamino-5-azido-1-chlorobenzene (dark green),
2-(4'-methylphenyl)amino-5-azidobenzene (dark green),
4-(2',5'-dimethoxyphenyl)amino-1-azidobenzene (dark green),
4-(4'-benzoylphenyl)amino-1-azidobenzene (dark green)
2-phenylamino-5-azido-1-nitrobenzene (dark brown),
2-(4'-diethylaminophenyl)amino-5-azido-1-nitrobenzene (dark brown),
2-(4'-ethoxyphenyl)amino-5-azidoacetophenone (dark brown),
4-(2',4'-dimethoxyphenyl)amino-3-diethylcarbamoyl-1-azidobenzene (dark brown),
2-phenylamino-5-azido-benzene sulfonic acid (dark brown),
2-(4'-ethoxyphenyl)amino-5-azido-N,N-dimethylaminosulfonyl benzene (dark brown),
2-(4'-methylphenyl)amino-5-azidomethylsulfonyl benzene (brown),
phenylester of 2-(3',5'-dimethylphenyl) amino-5-azidobenzene sulfonic acid (brown)
4-nitrophenyl ester of 2-phenylamino-5-azidobenzene sulfonic acid (brown),
4-(4'-bromophenyl)amino-3-(4''-methylphenyl)aminosulfonylazidobenzene (brown),
4-(4'-benzoylaminophenyl)amino-3-phenylsulfonylazidobenzene (dark brown),
4-(4'-benzoylaminophenyl) amino-3-phenylsulfonylazidobenzene (dark brown),
phenylester of 2-(4'-methylphenyl) amino-5-azidobenzoic acid (dark green),
4''-acetophenyl ester of 2-(4'-ethoxyphenyl) amino-5-azidobenzoic acid (dark green),
2'-naphthyl ester of 2-(4'-diethylaminophenyl) amino-5-azidobenzoic acid (dark green),
1'-naphthyl ester of 2-(4'-acetophenyl) amino-5-azidobenzoic acid (dark green),
(4''-tert-butyl) phenyl ester of 2-(2'-methylphenyl) amino-5-azidobenzoic acid (dark green),
4-(4'-hydroxyphenyl)amino-3-(N-phenylcarbozoyl)azidobenzene (dark brown),
4-phenylamino-3-(4'-chlorobenzoyl)-azidobenzene (dark brown),
4-(4'-nitrophenyl) amino-3-(4''-methylbenzoyl)-azidobenzene (brown), and
4-(4'-methoxyphenyl) amino-3-(4''-phenylnaphthoyl)azidobenzene (brown), On the other hand, if the [A] moiety in the photosensitive color-forming azido compound is a naphthalene ring, the —NH— group may be in either a 1-position or 2-position of the naphthalene ring and the $R_1$ and $R_2$ substituents may be in any positions of the naphthalene ring with respect to the —NH— group. In the above case, the photosensitive color-forming azido compound may be selected from the group consisting of the following compounds. In the following list, the color of the exposed compound is indicated in parenthesis.

2-(1'-naphthyl) amino-5-azidobenzoic acid (black),
2-(2'-naphthyl) amino-5-azidobenzoic acid (black),
2-(4'-methyl-1'-naphthyl) amino-5-azidobenzoic acid (black),
2-(4'-methoxy-1'-naphthyl) amino-5-azidobenzoic acid (black),
2-(4'-hydroxyl-1'-naphthyl) amino-5-azidobenzoic acid (bluish black),
2-(4'-diethylamino-1'-naphthyl) amino-5-azidobenzoic acid (black),
2-(4'-acetyl-1'-naphthyl) amino-5-azidobenzoic acid (black),
2-(6'-bromo-1'-naphthyl) amino-5-azidobenzoic acid (black),
methyl ester of 2-(1'-naphthyl) amino-5-azidobenzoic acid (dark green), 4-(4'-methyl-1'-naphthyl) amino-3-diethylcarbamoyl-1-azidobenzene (dark green),
4-(4'-methyl-1'-naphthyl) amino-3-diethylcarbamoyl-1-azidobenzene (dark green),
ethyl ester of 2-(4'-dimethylamino-1'-naphthyl) amino-5-azidobenzoic acid (dark green),
2-(4'-benzoylamino-1'-naphthyl) amino-5-azidobenzene sulfonic acid (dark green),
2-(1'-naphthyl) amino-5-azido-N,N-dimethylaminosulfonyl benzene (dark brown),
2-(1'-naphthyl) amino-5-azidotoluene (dark green),
2-(6'-chloro-1'-naphthyl) amino-5-azidotoluene (dark green),
2-(1'-naphthyl) amino-5-azidonitrobenzene (dark yellow),
2-(6'-bromo-1'-naphthyl) amino-5-azidoacetophenone (dark brown),
4-(4'-methoxy-1'-naphthyl) amino-3-methylsulfonyl-1-azidobenzene (dark brown),
2''-methylphenyl ester of 2-(4'-diethylamino-1'-naphthyl) amino-5-azidobenzene sulfonic acid (brown),
3''-methoxyphenyl ester of 2-(6'-bromo-1'-naphthyl) amino-5-azidobenzene sulfonic acid (brown),
1'''-naphthyl ester of 2-(1'-naphthyl) amino-5-azidobenzene sulfonic acid (brown),
4-(4'-methoxy-1'-naphthyl) amino-3-(5''-methylnaphthyl-amino) sulfonyl-azidobenzene (brown),
4''-methylphenyl ester of 2-(1'-naphthyl) amino-5-azidobenzoic acid (dark green), and
4-(1'-naphthyl) amino-3-(N-4''-bromophenyl) carbazoylazidobenzene (dark brown)

The photosensitive color-forming azido compounds of the formula (I) may be prepared by the following process. A primary amine compound of the formula (VI):

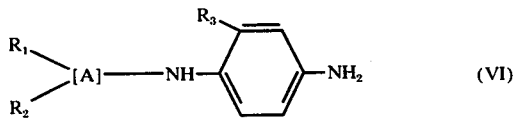

wherein [A], $R_1$, $R_2$ and $R_3$ are the same as defined hereinbefore, is dissolved or suspended in a solvent, for example, an aqueous solution of acetic acid, formic acid and dioxane. The solution is acidified by adding a small amount of hydrochloric acid or sulfuric acid and cooled to a temperature of 0° to 5° C. The amine compound of the formula (VI) is diazotized by adding dropwise an aqueous solution of sodium nitrite or nitrosylsulfuric acid to the solution. After the completion of diazotization, an aquious solution of an azido compound of an alkali metal, for example, sodium azido and potassium azido, is added to the above diazonium solution at a temperature of 0° to 5° C. The resultant azido compound is isolated by means of filtration, and dried. Generally, the azido compound is obtained at an yield of about 80% or more from the primary amine compound.

When a type of polymeric material, for example, a phenol novolak resin, is exposed to radiation rays in the presence of the photosensitive azido compound available for the present invention, the azido compound acts as a polymerization initiator so as to harden or insolubilize in solvent the polymeric material. Accordingly, the photosensitive color-forming layer in the photosensitive color-forming element of the present invention may further contain a polymeric material capable of hardening or being insolubilized in solvent when the polymeric material is exposed to radiation rays in the presence of the photosensitive color-forming azido compound. The polymeric material may be selected from the class consisting of phenol novolak resins, modified phenol novolak resins, styrenebutadiene copolymers, cyclized rubbers, polybutadiene and polyvinyl alcohols to which acrylonitrile or acrylamide is graftpolymerized. Generally, the alkali-soluble phenol novolak or modified phenol movolak resins are preferable as the polymeric materials to be blended with the photosensitive color-forming azido compound. The modified phenol novolak resins may be m-cresol, p-cresol, p-tert-butylphenol or cashew nut shell oil modified phenol novolak resin. The photosensitive color-forming azido compound may be blended in an amount of 5 to 30%, based on the weight of the polymeric material therewith.

The photosensitive color-forming azido compound may be also mixed with a solid material other than the abovementioned polymeric material, for example, colloidal silica, clay, titanium dioxide, calcium sulfate and barium sulfate.

In order to apply the photosensitive color-forming azido compound or its composition onto the support, the compound or composition is dissolved, in a concentration of 1 to 10%, in an organic solvent, preferably, a volatile organic solvent, for example, ethylene glycol monoethyl ether, ethylene glycol monoethyl ether acetate, cyclohexane, cyclohexanone, methylethyl ketone, dioxane, dimethylformamide, lower alkanols, dichloroethane, tetrahydrofurane, toluene, xylene and butyl acetate, and the solution is applied at a desired thickness onto one or two surfaces of the support by way of immersion, whirl-coating, brushing, doctor-blade, hopper-coating or spraying, and dried. The solution may further contain one or more anti-oxidizing agent, antistatic agent, polymerization accelerator, inhibitor, retarder, adhesive, activater and viscosity-controlling agent, in an amount of 0.01 to 30.0% based on the weight of the solid component in the solution, in response to the use of the element, type of the azido compound and type of the additive.

The support usable for the photosensitive color-forming element of the present invention may be in the form of film, sheet, fabric, web, plate or other shaped articles.

The support may consist of a cellulose ester, for example, cellulose diacetate, cellulose triacetate and cellulose acetate butylate; polyester, for example, polyethylene terephthalate; poly-α-olefin having, in its component monomer, 2 to 10 carbon atoms, for example, polyethylene and polypropylene; polystyrene; polycarbonate; paper; metal, for example, aluminium, zinc, copper and steel, and papers coated with one or more of the above-mentioned polymeric materials.

In the preparation of the photosensitive element of the present invention, it is unnecessary to add a coloring matter to the photosensitive layer, because the photosensitive azido compound can produce color by itself when the element is exposed to radiation rays. The photosensitive color-forming element of the present invention can be stored for a long period of time, for example, 6 months or more, without change in quality of the photosensitive layer.

In order to produce desired color images, the photosensitive color-forming layer of the element of the present invention is exposed for a predetermined time, 5 seconds to 5 minutes, in accordance with a predetermined pattern, to the rays from the sun and conventional artificial light sources, for example, carbon-arc lamp, mercury-arc lamp and xenon lamp. During the exposure, the exposed portions of the photosensitive layer produce color in response to the type of the azido compound contained in the photosensitive layer. If the photosensitive layer containes the polymeric material, the exposed portions of the photosensitive layer are hardened and insolubilized to solvent. Thereafter, the photosensitive layer is subjected to development with a developer liquid to remove the nonexposed portions of the layer. Generally, developer liquid is an aqueous solution containing an alkali compound, for example, sodium metasilicate and sodium hydroxide; or an organic solvent, for example, trichloroethylene, methyl alcohol, ethyl alcohol, toluene, xylene and methyl ethyl ketone. After the development, the photosensitive element is washed and dried. The images thus reproduced have a dark color, for example, black, brown, dark brown, dark green and dark blue black. If the photosensitive color-forming layer contains the polymeric material blended with the photosensitive azido compound, the resultant resinous color images have a high rigidity hardness, ink-receptivity (oleophilic property) and an excellent resistance to abrasion and to acid corrosion.

The photosensitive color-forming element of the present invention can be utilized as a copying sheet, or to produce a copying negative sheet, photo-resist, photo-relief, various printing plates (offset, presensitized and rotary photogravure plates), printed circuit boards and chemically etched metallic materials (Shadow mask of color Braun tube).

The present invention will be further illustrated by the following examples which are given by way of illustration and not as limitations of the scope of the present invention. In the examples, the parts and percentage are by weight unless otherwise stated.

PREPARATION OF AZIDO COMPOUND

EXAMPLE A 2-phenylamino-5-azidobenzoic acid was prepared by the following procedures.

10 parts of hydrochloric salt of 2-phenylamino-5-aminobenzoic acid was dissolved in 300 parts of water and 6 parts of concentrated hydrocholoric acid was added to the solution. An aqueous solution of 10% of sodium nitrite in an amount of 26.6 parts was added dropwise to the solution at a temperature of 0° to 5° C, and the mixture was maintained at the above-mentioned temperature for 1 hour while stirring, and thereafter, filtered. The filtrate was admixed with 33.2 parts of an aqueous solution of 10% of sodium azide. The admixture was stirred at a temperature of zero to 10° C for 1 hour to prepare the desired azido compound from the 2-phenylamino-5-adminobenzoic acid diazotized above. The azido compound was isolated by filtering the reaction admixture and drying. 9.0 parts of 2-phenylamino-5-azidobenzoic acid was obtained. The azido compound was melted and decomposed at a temperature of 160° C.

EXAMPLE B 2-phenylamino-5-azidobenzoic methyl ester was prepared by the following procedures.

The same procedures as in Example A were repeated except that 10 parts of 2-phenylamino-5-aminobenzoic methyl ester were used as the starting compound, and the aqueous solution of 10% sodium nitrite and the aqueous solution of 10% sodium azide were used in amount of 28 parts and 33.2 parts, respectively, 2-phenylamino-5-azidobenzoic methyl ester having a melting point of 64° to 65° C was obtained at an amount of 9.5 parts.

EXAMPLE C 2-(4'-Methoxyphenyl)amino-5-azidobenzoic acid was prepared by the following procedures.

34.3 parts of hydrochloride of 2-(4'-methoxyanilino)-5-aminobenzoic acid were dissolved in a mixture solvent consisting of 300 parts of glacial acetic acid, 180 parts of dioxane and 180 parts of water and 10 parts of concentrated hydrochloric acid was added to the solution. To the solution was added dropwise 81 parts of an aqueous solution containing 10% of sodium nitrite at a temperature of 0° to 5° C. After the completion of the addition, the mixture was stirred for 1 hour at the above-mentioned temperature and filtered. 98 parts of an aqueous solution containing 10% of sodium azide were added to the filtrate and the reaction mixture was stirred at a temperature of 0° to 10° C for 1 hour to prepare the desired azido compound from the 2-(4'-methoxyphenyl)amino-5-aminobenzoic acid diazotized above. The resultant azido compound which had been precipitated from the reaction mixture, was isolated by a filtration and dried. The yielding was 32.7 parts of 2-(4'-methoxyphenyl)amino-5-azidobenzoice acid having a melting (decomposing) point of 163° C.

EXAMPLE D

In order to prepare 2-(4'-methoxyphenyl)amino-5-azidobenzoic methylester, the following procedures were carried out.

By using 36.2 parts of hydrochloride of 2-(4'-methoxyphenyl)amino-5-aminobenzoic methyl ester, 10 parts of concentrated hydrochloric acid, 150 parts of water, 250 parts of glacial acetic acid, 150 parts of dioxane, 81 parts of an aqueous solution of 10% sodium nitrite and 98 parts of an aqueous solution of 10% sodium azide and following the procedures in Example C, 34.5 parts of 2-(4'-methoxyphenyl) amino-5-azidobenzoic methyl ester having a melting point of 103° to 104° C were obtained.

EXAMPLE E 2-(1'-naphthyl)amino-5-azidobenzoic acid was prepared by following the procedure outlined in Example C and using 38.9 parts of hydrochloride of 2-(1'-naphthyl)amino-5-aminobenzoic acid, 180 parts of water, 150 parts of glacial acetic acid, 150 parts of dioxane, 10 parts of concentrated hydrochloric acid, 81 parts of an aqueous solution of 10% sodium nitrite and 98 parts of an aqueous solution of 10% sodium azide. 27.6 parts of 2-(1'-naphthyl)amino-5-azidobenzoic acid was obtained, of which a melting (decomposing) point was 162° C.

EXAMPLE F

Methyl ester of 2-(1'-naphthyl) amino-5-azidobenzoic acid was prepared by the same procedures as in Example C except that 40.7 parts of hydrochloride of 2-(1'-naphthyl) amino-5-aminobenzoic acid, 200 parts of water, 150 parts of glacial acetic acid, 150 parts of dioxane, 10 parts of concentrated hydrochloric acid, 81 parts of an aqueous solution of 10% sodium nitrite and 98 parts of an aqueous solution of 10% sodium azide were used.

The methyl ester of 2-(1'-naphthyl) amino-5-azidobenzoic acid having a metling point of 99° to 103° C was yielded in an amount of 28.8 parts.

PREPARATION OF PHOTOSENSITIVE COLOR-FORMING ELEMENT

EXAMPLES 1, 2 AND 3

In Example 1, a photosensitive color-forming composition was prepared from 5 parts of 2-(4'-methylphenyl) amino-5-azidobenzoic acid and 8 parts of phenol novolak resin and dissolved in a solvent consisting of 60 parts of ethylene glycol monoethyl ether and 30 parts of cyclohexanone.

A surface of a zinc plate for photo-relief having a thickness of 1.0 mm was sand papered and treated with an aqueous solution of 5% of acetic acid to form a rough surface thereof. The zinc plate was washed with water and compeltely dried. Thereafter, the zinc plate was set up on a whirler.

The above-prepared photosensitive composition solution was applied onto the surface of the zinc plate while rotating the whirler at a velocity of 75 r.p.m. to coat the zinc plate surface with the photosensitive composition. The photosensitive composition solution was dried at a temperature of 80° C in a hot air drier to completely remove the solvent and form a thin film of the photosensitive composition. A photosensitive color-forming element was obtained. The photosensitive composition film was covered with a negative film having thereon a predetermined network pattern and exposed for 90 seconds to radiation rays from a 2 kw super high voltage mercury-arc lamp at a distance of 1 m. The exposed photosensitive composition film was developed by immersion in an aqueous solution of 2% of sodium metasilicate. During development, the non-exposed portions of the photosensitive composition film dissolved away and the exposed portions of the photosensitive composition film, which were hardened and colored black, were left on the zinc plate surface. After development, the photosensitive composition film was washed with water. Even after washing, the hardened photosensitive composition film remained firmly fixed to the zinc plate surface and had a rigidity sufficient for a photo-resist. Accordingly, the water-washed black images of the hardened photosensitive composition film formed on the zinc plate surface, can be subjected to etching, without any pre-treatment such as burning, to prepare a photo-relief for printing.

The photosensitive composition film formed on the zinc plate surface was very stable over a long period of storage to such a extent that even after 6 months storage, no change was found in the photosensitivity of the photosensitive composition film and even after 10 months, the time required to completely develop the stored photosensitive composition film was only 5 seconds longer than that required for the fresh photosensitive composition film.

In Example 2, operations identical to those in Example 1 were repeated using 2-(4'-methoxyphenyl) amino-5-azidobenzoic acid, instead of the 2-(4'-methylphenyl) amino-5-azidobenzoic acid. Similar results to those in Example 1 were obtained.

In Example 3, the same operations as in Example 1 were repeated except that ethyl ester of 2-(4'-acetaminophenyl) amino-5-azidobenzoic acid was used in place of the 2-(4-'-methylphenyl) amino-5-azidobenzoic acid. Similar results to those in Example 1 were obtained.

EXAMPLES 4, 5 AND 6

In Example 4, a base plate for a printed circuit board composed of a phenol-formaldehyde resin plate and a copper foil having a thickness of 0.3 mm and bonded to the phenolic resin plate, was sand papered and cleaned with trichloroethylene. A photosensitive composition solution was prepared using the following components and amounts.

| Component | Amount (part by weight) |
| --- | --- |
| 4-(2', 5'-dimethoxyphenyl) amino-1-axidobenzene | 1.5 |
| cyclized rubber (Pliolite NR-50, trademark by Goodyear Co., USA) | 9.0 |
| Xylene | 60 |
| Dioxane | 40 |

The photosensitive composition solution was applied onto the copper foil surface of the base plate with a spray gun and the layer of solution was dried to form a photosensitive composition film with thickness of 30 $\mu$ on the copper foil surface. A photosensitive color-forming element was obtained. A negative film having a negative pattern was superimposed on the photosensitive film and exposed to light for 2 minutes by means of a 2 kw super high voltage mercury-arc lamp spaced 1 m apart from the negative film. The non-exposed portions of the photsensitive film were removed with trichloroethylene. The developed element was subjected to etching by an 42° Be aqueous solution of ferric chloride at a temperature of 20° C. The resultant resin images were black, sharp in configuration and had few pin holes. The black resin resist film was sufficiently resistant to acid corrosion and abrasion for practical usage.

In each of Examples 5 and 6, operations identical to those in Example 4 were repeated using 2-(4'-methylphenyl) amino-5-azidotoluene (Example 5) or 2-(6'-bromo-1'-naphthyl) amino-5-azidoacetophenone. The same results as in Example 4 were obtained in each example.

EXAMPLES 7, 8 and 9

In Example 7, a binder plate for offset printing consisting of a stainless steel plate having been plated with a copper layer of a thickness of 2 $\mu$, was treated with an aqueous solution containing 0.5% of nitric acid to condition the surface thereof.

A solution of a photosensitive color-forming composition was prepared using the following components and amounts.

| Component | Amount (part by weight) |
|---|---|
| 2-(1'naphthyl) amino-5-azidobenzoic acid | 1.5 |
| metacresol novolak resin | 4.5 |
| Acrylic acid resin (Carbonset 525, trademark by Goodrich Chemical Co.) | 2.0 |
| diethylene glycol diethylether | 40.0 |
| ethylene glycol monoethyl ether acetate | 40.0 |
| cyclohexane | 20.0 |

The photosensitive composition solution was applied onto the copper-plated surface of the binder plate and dried to form a photosensitive film having a thickness of 20 $\mu$. The bimetal plate was superimposed upon a negative film having a network pattern and exposed, in a vacuum printing machine, for 1 minute, using a 2 kw super high voltage mercury-arc lamp spaced 1 m from the negative film. The exposed photosensitive film was developed with an aqueous developing solution of the following composition.

| Component | Amount (part by weight) |
|---|---|
| polyoxyethylene alkylphenylsulfate sodium salt (Emal NC, trademark by Kao-Atlas Co., Ltd., Japan) | |
| Sodium metasilicate | 4 |
| Water | 95 |

During the above development, the non-exposed portions of the photosensitive film were removed so as to expose portions of the copper surface covered by the non-exposed portions to the atmosphere. The exposed copper surface portions were etched with an etching solution of the following composition.

| Component | Amount (part by weight) |
|---|---|
| a 40 – 41° B' aqucous solution of calcium chloride | 1000 |
| Ferric chloride | 25 |
| Concentrated hydrochloric acid | 20 |

During the above etching, the exposed copper surface portions were removed so as to expose portions of the stainless steel surface covered by the copper layer to the atmosphere. The exposed stainless steel surface portions were coated with a solution of 1000 parts of a 9° Be aqueous solution of a gum alabi, 200 parts of a 2.5% aqueous solution of tannic acid and 14 parts of a 95% phosphoric acid to desensitize the exposed surface portions to fatty substance.

The resultant black bimetal plate for printing had a high durability for a long period of printing, in that more than 50,000 pieces of high quality paper were printed with a single bimetal printing plate.

In Examples 8 and 9, the same operations in Example 7 were carried out using, instead of the 2-(1'-naphthyl) amino-5-azidobenzoic acid, ethyl ester of 2-(2', 4'-dimethylphenyl) amino-5-azidobenzoic acid (Example 8) and 4-(4'methoxy -1'-naphthyl) amino-3-methylsulfonyl-1-azoidobenzene (Example 9). The same results as in Example 7 were obtained in each example.

EXAMPLE 10

The blade of an electric shaver was produced by the following method.

A photosensitive composition consisting of 3 parts of 2-(4'-chlorophenyl) amino-5-azidoanisole and 50 parts of sytrene-butandiene rubber was dissolved in a mixture solvent of 600 parts by volume of xylene and 400 parts by volume of cyclohexane to prepare a photosensitive composition solution. A steel plate with a thickness of 0.08 mm was immersed in the photosensitive composition solution and slowly withdrawn from the solution. Thereafter, the steel plate was set up on a whirler and rotated to remove any excess solution from the steel plate surface. After drying the solution, both the upper and lower surfaces of the steel plate were coated with a photosensitive composition film having a thickness of above 25 $\mu$. A chromium mask was superimposed on one surface of the steel plate coated with the photosensitive composition film and exposed for 100 seconds to 30A arc lamp. Thereafter, the chromium mask was superimposed on the opposite surface of the steel plate at a position accurately corresponding to the position of the chromium mask superimposed on the previous surface, and subjected to the same exposure as mentioned above.

The exposed photosensitive composition film was developed with trichloroethylene. Thereafter an aqueous solution of 6% of nitric acid was sprayed onto the two surfaces of the steel plate to etch it in accordance with the pattern of the chromium mask. The etched steel plate was neutralized and washed with water and, thereafter, plated with chromium. A blade of an electric shaver was obtained.

EXAMPLES 11, 12 and 13

In Example 11, a photosensitive composition consisting of 2.0 parts of 2-(4'-acetylphenyl) amino-5-azidobenzoic acid and 3.0 parts of colloidal silica was dissolved in a solvent consisting of 60 parts of ethylene glycol monoethyl ether acetate and 40 parts of methyl ketone to prepare a photosensitive composition solution. The solution was uniformly coated on a piece of 100% rag paper and dried to form a photosensitive color-forming element. A semiopaque negative film having thereon transparent images to be reproduced on the paper was overlaid on the photosensitive element. The photosensitive element was exposed for 2 minutes through the negative film to radiation rays from a 200 W super high voltage mercury lamp at a distance of 1 m. The exposed portions of the photosensitive element were colored black in the patterns of the negative film. The formed images on the photosensitive element were fixed in a fixing solution consisting of 4.0 parts by volume of sodium metasilicate, 0.5 parts by volume of sodium lauryl sulfate and 95 parts by volume of water, and washed with water. Stable and sharp black images were obtained on the paper.

In Examples 12 and 13, the same operations as in Example 11 were carried out using 2-(4'-diethylaminophenyl) amino-5-azidobenzoic acid (Examples 12) and 2-(4'methoxy - 1'-naphthyl) amino -5-azidobenzoic acid (Example 13), instead of the 2-(4'-acetylphenyl) amino-5-azidobenzoic acid. In each of the examples, the same stable and sharp black images as in Example 11 were obtained.

EXAMPLES 14, 15 and 16

In Example 14, a photosensitive compound solution was prepared by dissolving 1.5 parts of 4-(2', 5-dimethoxyphenyl) amino-1-azidobenzene in a mixture solvent consisting of 60 parts of xylene and 40 parts of dioxane. The solution was uniformly applied onto a surface of the piece of filter paper and, then, dried to form a photosensitive color-forming element. The same negative film as used in Example 11 was overlaid on the photosensitive element surface. The photosensitive surface of the element was exposed for 1 minute to radiation rays which were rich in ultraviolet rays from a 250 W high voltage mercury lamp through the negative film. Black images in the same patterns as on the negative film were formed on the photosensitive surface of the element. The non-exposed portion of the photosensitive surface of the element was removed away by means of trichloroethylene. Thereafter, the element was washed and dried. Stable and sharp black images were maintained on the paper surface.

In Examples 15 and 16, the same procedures as in Example 14 were carried out except that the photosensitive compound used was 2-(4'-methylphenyl) amino-5-azidotoluene (Example 15) and 2-(6'-bromo-1'-naphthyl) amino-5-azidoacetophenone (Example 16). In each of the examples, the same black, stable, sharp images were produced on the paper.

EXAMPLES 17 through 20

In Example 17, a photosensitive composition consisting of 0.2 parts of 2-(4'-methylphenyl) amino-5-azidobenzoic acid and 0.8 parts of phenol novolak was dissolved in 10 parts of methylethyl ketone. The solution was applied onto a surface of an aluminum plate set up on a rotating whirler, and dried at a temperature of 80° C in a dryer through which hot air flows to prepare a photosensitive color-forming element having thereon a photosensitive color-forming film layer. The element was imagewisely exposed for 2 minutes to radiation rays which were rich ultraviolet rays from a 250 W high voltage mercury lamp. Black images were produced on the element surface. The exposed element was subjected to development with an aqueous solution containing 2% of sodium metasilicate, to remove the non-exposed portions of the photosensitive film layer, washed with water and dried. Stable and sharp black images were obtained on the aluminum plate surface.

In Examples 18, 19 and 20, the same operations as in Example 17 were repeated using, instead of the 2-(4'-methylphenyl) amino-5-azidobenzoic acid, 2-(4'-methoxyphenyl) amino-5-azidobenzoic acid (Example 18), 4-(methylphenyl) amino-1-azidobenzene (Example 19) and ethyl ester of 2-(4'-acetaminophenyl) amino-5-azidobenzoic acid (Example 20). In each of the examples, the same black, stable, sharp images were obtained.

EXAMPLES 21, 22 and 23

In Example 21, a photosensitive color-forming composition consisting of 1.5 parts of 2-(1'-naphthyl) amino-5-azidobenzoic acid and 6.0 parts of metacresol novolak resin was coated on a surface of a support consisting of polyethylene terephthalate film by means of a doctor blade at a thickness of the wet coating of 0.006 inch, to prepare a photosensitive color-forming element having a photosensitive color-forming coating layer. The photosensitive color-forming coating layer was imagewisely exposed for 1 minute to a 1200 W high voltage mercury lamp at a distance of 1 m. The non-exposed portions of the photosensitive color-forming coating was removed with a developing aqueous solution containing 1% of sodium hydroxide. The element was washed with water and dried. Black images were firmly fixed to the support surface.

In Examples 22 and 23, the same procedures as in Example 11 were repeated using, in place of the 2-(1'-naphthyl) amino-5-azidobenzoic acid, ethyl ester of 2-(2', 4'-dimethylphenyl) amino-5-azidobenzoic acid (Example 22) and 4-(4'-methoxy-1'-naphthyl) amino-3-methylsulfonyl-1-azidobenzene. In each example, the same black images as in Example 21 were produced.

EXAMPLE 24, 25 and 26

In Example 24, a photosensitive composition, consisting of 0.6 parts of 2-(4'-hydroxyl-1'-naphthyl) amino-5-azidobenzoic acid, 2.0 parts of metacresol novolak resin and 0.4 parts of acrylic acid resin (Carboset 525: trademark by Goodrich Chemical Co.), was dissolved in a mixture solvent consisting of 4.0 parts of diethylene glycol dimethyl ether and 2.0 parts of cyclohexane. The photosensitive composition solution was coated on a surface of a support consisting of a polyethylene terephthalate film at a thickness of 0.0006 inches in wet condition, by means of a doctor blade, and dried to prepare a photosensitive color-forming element having thereon a photosensitive color-forming coating layer. The photosensitive coating layer was imagewisely exposed for 1 minute to a 2000 W super high voltage mercury lamp at a distance of 1 m. The non-exposed portions of the photosensitive coating layer was removed in a developer consisting of ethyl alcohol. The element was washed with water and dried. Dark blue black images were produced on the support surface.

In Examples 25 and 26, the same procedures as in Example 25 were repeated using, instead of the 2-(4'-hydroxy-1'-naphthyl) amino-5-azidobenzoic acid, 2-(4'-hydroxyphenyl) amino-5-azidobenzoic acid (Example 25) and 4-(2', 5'-dimethoxyphenyl) amino-3-diethylcarbamoyl-1-azidobenzene (Example 26). In each example, black images were produced on the support.

Example 27, 28 and 29

In Example 27, in order to prepare a photo-relief, the same procedures as in Example 1 were repeated using, as the photosensitive compound, phenyl ester of 2-(3', 5'-dimethylphenyl) amino-5-azidobenzene sulfonic acid.

The photosensitive composition film formed on the zinc plate surface could maintain its photosensitivity without diminution even after 6 months storage. Further, even after 10 months storage, the time required for developing the stored photosensitive element was only about 5 seconds longer than that of a fresh element. When the photosensitive composition film was imagewisely exposed to the 2KW super high voltage mercury lamp, the exposed portions of the film were completely hardened and colored brown. In Examples 28 and 29, the same operations as in Example 27 were carried out by using, as the photosensitive compound, (4'-nitrophenyl) ester of 2-phenylamino-5-azidobenzene sulfonic acid (Example 28) and (4''-acetophenyl) ester of 2-(4'-ethoxyphenyl) amino-5-azidobenzoic acid. In each example, the same results as that of Example 27 were obtained except that the color of the exposed images in Example 28 was brown and that in Example 29 was dark green

EXAMPLES 30, 31 and 32

In Example 30, procedures indentical to those in Example 4 were carried out by using, as the photosensitive compound, phenyl ester of 2-(4'-methylphenyl) amino-5-azidobenzoic acid. The resultant resinous images of the hardened photosensitive composition was dark green and had high resistances to acids and abrasion. The images were sharp and included few pin holes.

In Examples 31 and 32, the same operations as in Example 30 were repeated by using, as the photosensitive compound, (4"-test-butyl)-phenyl ester of 2-(4'-acetophenyl) amino-5-azidobenzoic acid (Example 31) and 4-(4'-methoxyphenyl) amino-3-(4"-ethylnaphthoyl)-azidobenzene (Example 32). The hardened resinous images in Example 31 were dark green and those in Example 32 were brown. The images had the same quality as those in Example 30.

EXAMPLE 33

In example 33 procedures identical to those in Example 7 were carried out by using 4-phenylamino-3-(4'-chlorobenzoyl)-azidbenzene as the photosensitive color-forming compound. After exposure to the super high voltage mercury lamp, the exposed portions of the photosensitive composition film layer were completely hardened and colored dark brown. The resultant dark brown bimetal plate for printing had an excellent durability for printing. Prints having excellent quality were obtained with no diminution of image sharpness, clarity or density even after 50,000 impressions.

EXAMPLE 34

In example 34 procedures identical to those in Example 10 were effected by using 4-(4'benzoylamino)-phenylamino-3-(phenylsulfonyl)-azidobenzene as the photosensitive color-forming compound. After exposure was completed, a dark brown resinous film was formed in each surface of the steel plate. The same results in Example 10 were obtained.

EXAMPLES 35 and 36

In Example 35, operations identical to those in Example 11 were effected using 1'-naphthyl ester of 2-(4'-acetophenyl) amino-5-azidobenzoic acid as the photo-sensitive color-forming compound. By the exposure and fixing operations, dark brown images were formed on the paper. The images had excellent quality in sharpness, clarity and density.

In Example 36, the same procedures as in Example 35 were repeated using 4-(4'-methoxynaphthyl) amino-3 (5"-methyl-naphtyl) amino-sufonyl -azidobenzene as the photosensitive color-forming compound. The resultant images were brown and had the same quality as in Example 35.

EXAMPLES 37 and 38

In Example 37, the same procedures as in Examples 14 were carried out using 4'-methylphenyl ester of 2-(1'-naphthyl) amino-5-azidobenzoic acid as the photosensitive color-forming compound. By the exposure, dark green images were produced on the filter paper.

In Example 38, the same operations as in Example 37 were repeated using 4-(4'-nitrophenyl) amino-3-(4"-methylbenzoyl)-azidobenzene as the photosensitive colorforming compound. By the exposure, brown images were formed on the filter paper.

EXAMPLE 39

In Example 39 procedures identical to those in Example 17 were carried out using 4-(1'-naphthyl) amino-3- (N-4"-bromophenyl)-carbazoyl -azidobenzene as the photosensitive color-forming compound. After the exposure, dark brown resinous images where completely hardened and and firmly fixed on the aluminum plate.

EXAMPLES 40, 41 and 42

In Example 40, the same operations as in Example 21 were carried out using (4"-tert-butyl)-phenyl ester of 2-(2'-methylphenyl) amino-5-azidobenzoic acid as the photosensitive color-forming compound. After exposure, developing and washing, there were dark green resinous images on the support surface.

In Example 41 and 42, procedures identical to those in Example 40 were repeated using 4-(4'-methoxyphenyl) amino-3-(4"-ethylnaphthoyl)-azidobenzene (Example 41) and 1"-naphthyl ester of 2-(1'-naphthyl) amino-5-azidobenzene sulfonic acid (Example 42), as the photosensitive colorforming compound. In both the examples, brown resinous images were obtained.

EXAMPLES 43 and 44

In both Examples 43 and 44 procedures identical to those in Example 24 were carried out except that (2"-methylphenyl) ester of 2-(4'-diethylamino-1'-naphthyl) amino-5-azidobenzene sulfonic acid in Example 43 and (3"-methoxy-phenyl) ester of 2-(6'-bromo-1'-naphthyl) amino-5-azidobenzene sulfonic acid in Example 43 and (3"-methoxyphenyl)ester of 2-(6'-bromo-1'-naphthyl) amino -5-azidobenzene sulfonic acid in Example 44 were used as the photosensitive color-forming compound. As a result of exposure and development, brown resinous images were formed in both the examples.

What we claim is:

1. A photosensitive color forming element comprising a support and a photosensitive color-forming layer coated on said support and containing therein at least one photosensitive color forming azido compound of the formula (I):

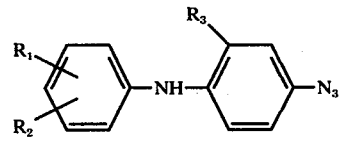

wherein $R_1$ and $R_2$ respectively represent a substituent selected from the group consisting of hydrogen and halogen atoms and alkyl, alkoxyl, dialkylamino, acylamino, and hydroxyl radicals, and are respectively in 2 - and 4 - positions, 3 - and 5 - positions or 2 - and 5 - positions of said benzene ring with respect to said -NH- group of said benzene ring, and $R_3$ represents an alkylcarboxyl radical.

2. A photosensitive color-forming element as claimed in claim 1 wherein said photosensitive color-forming azido compound is selected from the group consisting of methyl ester of 2-phenylamino-5-azidobenzoic acid, methyl ester of 2-(4'-methoxyphenyl) amino-5- azidobenzoic acid, ethyl ester of 2-(2′,4′-dimethylpehnyl) amino-5-azidobenzoic acid, and ethyl ester of 2-(4′-acetaminoanilino)-5-azidobenzoic acid.

3. A photosensitive color-forming element as claimed in claim 1, wherein said photosensitive color-forming layer further contains a polymeric material capable of hardening or being non-solubilized in solvent when said polymeric material is exposed to radiation rays in the presence of said photosensitive color-forming azido compound.

4. A photosensitive color-forming element as claimed in claim 3, wherein said polymeric material is selected from the class consisting of phenol novolak resins and, modified phenol novolak resins modified with a substance selected from the group consisting of m-cresol, p-cresol, p-tert-butyphenol or cashew nut shell oil.

5. A photosensitive color-forming element as claimed in claim 1, wherein said photosentive color-forming azido compound is in an amount of at least 5% based on the weight of said photosensitive color-forming layer.

6. A photosensitive color-forming element as claimd in claim 3, wherein said photosensitive color-forming azido compound is in an amount of 5 to 30% based on the weight of said polymeric material.

7. A photosensitive color-forming element as claimed in claim 1, wherein said alkyl radical as said $R_1$ and $R_2$ has 1 to 4 carbon atoms.

8. A photosensitive color-forming element as claimed in claim 1, wherein said alkoxyl radical as said $R_1$ and $R_2$ has 1 to 4 carbon atoms.

9. A photosensitive color-forming element as claimed in claim 1, wherein the alkyl groups in said dialkylamino radical as said $R_1$ to $R_2$ respectively have 1 to 4 carbon atoms.

10. A photosensitive color-forming element as claimed in claim 1, wherein the acyl group in said acylamino radical as said $R_1$ and $R_2$ has 2 to 7 carbon atoms.

11. A photosensitive color-forming element as claimed in claim 1, wherein the alkyl group in said alkylcarboxyl radical as said $R_3$ has 1 to 4 carbon atoms.

12. A photosensitive color-forming element as claimed in claim 3 wherein said support consists of cellulose diacetate, cellulose triacetate, cellulose acetate butylate, polyethylene, polypropylene, polystyrene, polyethylene terephtalate, polycarbonate, zinc, aluminum, steel, paper, and papers coated with one or more of said polymeric materials.

* * * * *

UNITED STATES PATENT OFFICE
CERTIFICATE OF CORRECTION

Patent No. 4,019,907  Dated April 26, 1977

Inventor(s) Takahiro Tsunoda, et al.

It is certified that error appears in the above-identified patent and that said Letters Patent are hereby corrected as shown below:

In column 1, line 16, after "an" delete "azu" and insert therefore -- azo --.

In column 10, in the table beginning with line 25 and specifically at the second line of the table, after "1-" delete "axidobeuzene" and insert therefore -- azidobenzene --.

In column 10, line 46, after "Be" insert -- ' --, such that it reads "Be'".

In column 11, in the table beginning with line 40, and specifically at the first line of the table, after "40-41°" delete "B'" and insert therefore -- Be' --.

In column 11, line 53, after "Be", insert -- ' -- such that it reads "Be'".

In column 12, lines 51-52, after "a" delete "200W" and insert therefore -- 2000W --.

UNITED STATES PATENT OFFICE
CERTIFICATE OF CORRECTION

Patent No. 4,019,907    Dated April 26, 1977

Inventor(s) Takahiro Tsunoda, et al.

It is certified that error appears in the above-identified patent and that said Letters Patent are hereby corrected as shown below:

In column 15, line 27, after ".(4'-chlorobenzoyl)" delete "azidbenzene" and insert therefore -- azidobenezene --.

Signed and Sealed this

Fourth Day of April 1978

[SEAL]

Attest:

RUTH C. MASON
Attesting Officer

LUTRELLE F. PARKER
Acting Commissioner of Patents and Trademarks